United States Patent
Jing et al.

(10) Patent No.: US 12,369,774 B2
(45) Date of Patent: Jul. 29, 2025

(54) ENDOSCOPE FORCEPS ELEVATOR, ENDOSCOPE DISTAL END AND DUODENOSCOPE SYSTEM

(71) Applicant: SONOSCAPE MEDICAL CORP., Guangdong (CN)

(72) Inventors: Feng Jing, Guangdong (CN); Keduan Xu, Guangdong (CN); Gongan Wu, Guangdong (CN)

(73) Assignee: SONOSCAPE MEDICAL CORP., Guangdong (CN)

( * ) Notice: Subject to any disclaimer, the term of this patent is extended or adjusted under 35 U.S.C. 154(b) by 740 days.

(21) Appl. No.: 17/622,735

(22) PCT Filed: May 26, 2020

(86) PCT No.: PCT/CN2020/092221
§ 371 (c)(1),
(2) Date: Dec. 24, 2021

(87) PCT Pub. No.: WO2020/259177
PCT Pub. Date: Dec. 30, 2020

(65) Prior Publication Data
US 2022/0160210 A1    May 26, 2022

(30) Foreign Application Priority Data
Jun. 24, 2019  (CN) .......................... 201910550770.6

(51) Int. Cl.
*A61B 1/00*  (2006.01)
*A61B 1/018*  (2006.01)
(Continued)

(52) U.S. Cl.
CPC .......... *A61B 1/00098* (2013.01); *A61B 1/018* (2013.01); *A61B 1/05* (2013.01);
(Continued)

(58) Field of Classification Search
CPC ....... A61B 1/00098; A61B 1/018; A61B 1/05; A61B 1/06; A61B 1/126; A61B 17/29
See application file for complete search history.

(56) References Cited

U.S. PATENT DOCUMENTS

2012/0078041 A1* 3/2012 Kitano ............... A61B 1/00098
                                                                    600/107
2015/0173711 A1   6/2015 Hiraoka
(Continued)

FOREIGN PATENT DOCUMENTS

CN        101073492 A    11/2007
CN        102469922 A    5/2012
(Continued)

OTHER PUBLICATIONS

International Search Report for PCT/CN2020/092221 mailed Aug. 26, 2020, ISA/CN.

Primary Examiner — John P Leubecker
Assistant Examiner — Li-Ting Song
(74) Attorney, Agent, or Firm — Yue (Robert) Xu

(57) ABSTRACT

Disclosed are an endoscope forceps elevator, an endoscope distal end and a duodenoscope system. The bottom of the endoscope forceps elevator is in communication with an instrument channel and the endoscope forceps elevator is provided with a hinge part configured to be hinged with an endoscope distal end base; a positioning groove adapted to an instrument to be positioned is provided at the top of the endoscope forceps elevator; and a cutting edge and a guide surface are provided at a side of the endoscope forceps elevator, and the guide surface is located between the positioning groove and the cutting edge. The cutting edge is movable in contact with the inner side surface of the distal end base so as to guide the instrument to be positioned in a first deflected and extended state onto the guide surface.

20 Claims, 14 Drawing Sheets

(51) Int. Cl.
*A61B 1/05* (2006.01)
*A61B 1/06* (2006.01)
*A61B 1/12* (2006.01)
*A61B 17/29* (2006.01)

(52) U.S. Cl.
CPC ............... *A61B 1/06* (2013.01); *A61B 1/126* (2013.01); *A61B 17/29* (2013.01)

(56) References Cited

U.S. PATENT DOCUMENTS

| | | | |
|---|---|---|---|
| 2020/0008778 A1* | 1/2020 | Morimoto | A61B 8/445 |
| 2020/0281446 A1* | 9/2020 | Morimoto | A61B 1/018 |
| 2020/0315428 A1* | 10/2020 | Harada | A61B 1/00112 |
| 2022/0160210 A1* | 5/2022 | Jing | A61B 1/126 |
| 2023/0122213 A1* | 4/2023 | Harada | A61B 8/12 600/471 |
| 2023/0363624 A1* | 11/2023 | Yajima | A61B 17/29 |
| 2023/0389785 A1* | 12/2023 | Inoue | A61B 1/00042 |

FOREIGN PATENT DOCUMENTS

| | | |
|---|---|---|
| CN | 104619265 A | 5/2015 |
| CN | 106691361 A | 5/2017 |
| CN | 109589084 A | 4/2019 |
| CN | 110179431 A | 8/2019 |
| JP | 2001333878 A | 12/2001 |
| JP | 2005304586 A | 11/2005 |

* cited by examiner

ENDOSCOPE FORCEPS ELEVATOR, ENDOSCOPE DISTAL END AND DUODENOSCOPE SYSTEM

The present disclosure is a national phase application of PCT international patent application PCT/CN2020/092221, filed on May 26, 2020 which claims priority of Chinese Patent Application No. 201910550770.6, titled "ENDOSCOPE FORCEPS ELEVATOR, ENDOSCOPE HEAD END AND DUODENOSCOPE SYSTEM", filed with the China National Intellectual Property Administration on Jun. 24, 2019, which is incorporated herein by reference in its entirety.

FIELD

The present disclosure relates to the technical field of medical instruments, and in particular to an endoscopic forceps elevator, an endoscopic distal end, and a duodenoscope system.

BACKGROUND

Cancer is a general term for a major malignant tumor. Cancer cells have a character of unlimited and endless proliferation, which causes a large amount of nutrients in a body of patient to be consumed. China is a major country prone to gastrointestinal diseases, and has been in trouble with a low detection rate and a high mortality of gastrointestinal diseases for a long time. At present, the most effective way to fight cancer is recognized internationally as early detection, early diagnosis, and early treatment. Early cancer diagnosis is a diagnosis and treatment method specifically for early cancer patients. Endoscopic diagnosis is the most representative early diagnosis of gastrointestinal cancer, which has an advantage of observing and taking pictures at the same time, and is widely used in clinical practice.

A duodenoscopy refers to a method that uses a duodenoscope to perform duodenoscope diagnosis, which can be applied to diagnose duodenal, liver, gallbladder or pancreatic diseases, and can also be applied to adjuvant treatment of the digestive system. When performing a treatment of the digestive system or pancreaticobiliary system by means of a duodenoscope, in addition to the use of endoscope to perform the treatment of angiographic diagnosis to the digestive tract, bile duct or pancreatic duct, there is further a treatment of recovering gallstones presented in the common bile duct by balloons or holding treatment instrument.

ERCP is endoscopic retrograde cholangiopancreatography. During the ERCP operation, the duodenoscope is inserted into a descending portion of the duodenum to find the duodenal papilla, and a catheter is inserted via the inside of the instrument channel to the papilla opening, and then a contrast agent is injecting to take X-ray images so as to show a pancreaticobiliary duct, and surgical operations such as incision and stone recovery are performed on the pancreaticobiliary duct.

When a treatment instrument needs to be replaced during the ERCP operation, a guide wire is inserted inside the treatment instrument, a distal portion of the guide wire remains of being inserted into the papilla, and a subsequent treatment instrument is guided by the guide wire to be inserted into the papilla.

The endoscopic distal end portion includes a distal end base and a forceps elevator, and the forceps elevator is located in an accommodating space of the distal end base. Extension angles of the catheter, guide wire or other treatment instruments can be controlled by the lifting and lowering of the forceps elevator, and the catheter or other treatment instruments can be inserted into the papilla to reach the pancreatic duct or bile duct by cooperating with the bending and rotation of an endoscope.

As shown in FIG. 1, in a case that the guide wire extends into the accommodating space at the endoscopic distal end portion via the instrument channel, an extending-out position of the guide wire is unfixed.

If an extending-out state of the guide wire is shown by the thick line a, the guide wire normally extends out of the endoscopic distal end portion via the instrument channel.

If the extending-out state of the guide wire is shown by the thick line b, the extending-out position of the guide wire is right deflected. This is because when the endoscopic distal end portion penetrates into a human body, it is blocked by internal organs of the left human body, which results in the extending-out position being right deflected. At this time, the guide wire is in a right deflective extending-out state.

If the extending-out state of the guide wire is shown by the thick line c, the extending-out position of the guide wire is left deflected. This is because when the endoscopic distal end portion penetrates into the human body, it is blocked by internal organs of the right human body, which results in an extending-out position being left deflected. At this time, the guide wire is in a left deflective extending-out state.

In a case that an extending-out state of the guide wire is a deflective extending-out state, the guide wire is not able to extend against a guiding groove of the forceps elevator and continue to extend into a positioning bayonet at the top of the forceps elevator, but the guide wire is deflected from the forceps elevator and extends out of the accommodating space. In that case, the guide wire cannot be positioned by the forceps elevator either before or after the forceps elevator is lifted, so that the guide wire cannot be fixed. Therefore, other treatment instruments also cannot be guided by the guide wire to a predetermined position after extending out of the instrument channel, and surgery cannot be performed.

Similarly, during a treatment process, the extending-out states of the catheter or other treatment instruments are the same with that of the guide wire.

Therefore, in the conventional technologies, a technical problem to be urgently solved by those skilled in the art is to effectively and accurately clamp and fix the instruments to be positioned such as guide wire, catheter, or other treatment instruments when deflectively extending out, so as to prevent these instruments from coming out of a papilla and being moved to the inside of the papilla.

SUMMARY

In view of this, an object of the present disclosure is to provide an endoscopic forceps elevator, an endoscopic distal end, and a duodenoscope system, which are configured to effectively and accurately clamp and fix the guide wire, the catheter, or other treatment instruments deflectively extending out, so as to obtain the objects of avoiding the instrument to be positioned from coming out of a papilla and being moved to the inside of the papilla.

In order to achieve the above objects, the following technical solutions are provided according to the present disclosure.

An endoscopic forceps elevator, where the bottom of the endoscopic forceps elevator is in communication with an instrument channel, and a hinge portion for hinging with a distal end base of an endoscope is arranged at the bottom of the endoscopic forceps elevator;

a positioning groove adapted to an instrument to be positioned is arranged at the top of the endoscopic forceps elevator;

a shearing edge and a guiding surface are provided at a side edge of the endoscopic forceps elevator, and the guiding surface is located between the positioning groove and the shearing edge;

during a lifting process of the endoscopic forceps elevator, the shearing edge is able to move against an inner surface of the distal end base to guide the instrument to be positioned in a first deflective extending-out state onto the guiding surface; the guiding surface is configured to guide the instrument to be positioned into the positioning groove, and the positioning groove is configured to cooperate with an abutting and fixing member to clamp and fix the instrument to be positioned.

In an embodiment, in the above endoscopic forceps elevator, an outer notch of the positioning groove is a positioning bayonet located at the top end of the endoscopic forceps elevator; a guiding groove in communication with the positioning bayonet and the instrument channel, respectively, is arranged between the positioning bayonet and the instrument channel; before the endoscopic forceps elevator being lifted, the instrument to be positioned is guide into the positioning bayonet by the guiding groove and position-limited laterally.

Preferably, in the above endoscopic forceps elevator, the positioning groove is in a strip-shaped groove structure, one side of the positioning groove intersects with the guiding surface to form a first transition edge 112 or a transition surface, and the other side of the positioning groove intersects with the guiding groove to form a second transition edge 114.

An endoscopic distal end includes a distal end base and a forceps elevator, where the forceps elevator is the endoscopic forceps elevator described above.

In an embodiment, in the above endoscopic distal end, the distal end base includes a first mounting portion, a second mounting portion and an accommodating space for accommodating the forceps elevator; the bottom of the accommodating space is in communication with the instrument channel, and the two sides of the accommodating space are a first inner side surface of the first mounting portion and a second inner side surface of the second mounting portion, respectively; a front surface of the first mounting portion is a working surface for installing functional devices, and the working surface intersects with the first inner side surface; a protruding wall protruding outside the working surface is provided on the bottom of the working surface close to the accommodating space, and an inner side surface of the protruding wall is coplanar with the first inner side surface, and both of which are inner side surfaces of the distal end base;

during a lifting process of the forceps elevator, the shearing edge is able to be moved against the inner side surface of the protruding wall to guide the instrument to be positioned in the first deflective extending-out state onto the guiding surface.

In an embodiment, in the above endoscopic distal end, an outer edge of the protruding wall includes an inclined edge with a gradually decreasing protrusion height, and a part of the inclined edge with the highest protrusion height is closer to the bottom of the accommodating space than a part of the inclined edge with the lowest protrusion height.

In an embodiment, in the above endoscopic distal end, a first mounting surface, a second mounting surface and a third mounting surface are arranged on the working surface in sequence along the axial direction;

the first mounting surface is located at a radial outer side of the bottom of the accommodating space;

the third mounting surface is located at a radial outer side of the top of the accommodating space;

the second mounting surface is an inclined surface located between the first mounting surface and the third mounting surface;

a distance between the first mounting surface and a center plane of the endoscopic distal end is smaller than a distance between the third mounting surface and the center plane of the endoscopic distal end, and the protruding wall is provided on the first mounting surface.

In an embodiment, in the above endoscopic distal end, the functional devices include:

a nozzle of a water vapor system, which is mounted on the first mounting surface;

an objective lens of an imaging system, which is mounted on the second mounting surface;

a lens of an illumination system, which is mounted on the third mounting surface.

In an embodiment, in the above endoscopic distal end, an included angle between an inner side surface of the distal end base and the guiding surface is greater than 90 degrees and less than 180 degrees.

In an embodiment, in the above endoscopic distal end, the abutting and fixing member is located at the bottom of the accommodating space, and an abutting surface of the abutting and fixing member includes a first abutting surface and a second abutting surface;

the first abutting surface is configured to cooperate with the positioning groove to clamp and fix the instrument to be positioned;

the shearing edge is arranged at one side of the endoscopic forceps elevator, and a side edge positioning portion is arranged at the other side of the endoscopic forceps elevator; after the endoscopic forceps elevator being lifted, the side edge positioning portion is configured to cooperate with the second abutting surface to clamp and fix the instrument to be positioned in a second deflective extending-out state.

In an embodiment, in the above endoscopic distal end, the second abutting surface and the second inner side surface form a clamping groove for accommodating the side edge positioning portion; in a case that the instrument to be positioned is in the second deflective extending-out state, after the forceps elevator being lifted, the instrument to be positioned is configured to be abutted against the side edge positioning portion so as to be fixed in the clamping groove.

In an embodiment, in the above endoscopic distal end, an included angle between the first abutting surface and a center axis of the endoscopic distal end is greater than zero.

In an embodiment, in the above endoscopic distal end, the second abutting surface is a flat surface, a curved surface, or a stepped surface.

A duodenoscope system, where the duodenoscope system is provided with the endoscopic distal end described above.

It can be seen from the above technical solutions that, in a case that the instrument to be positioned such as the guide wire, the catheter, or other treatment instruments deflectively extends out, the endoscopic forceps elevator, the endoscopic distal end and the duodenoscope system provided according to the present disclosure are configured to adjust the instrument to be positioned back to the positioning groove, so as to obtain the objects of avoiding the instrument to be positioned from coming out of a papilla and of being moved to the inside of the papilla and ensuring the successful operation of surgery.

BRIEF DESCRIPTION OF THE DRAWINGS

For more clearly illustrating embodiments of the present disclosure or the technical solutions in the conventional technology, drawings referred to for describing the embodiments or the conventional technology will be briefly described hereinafter. Apparently, drawings in the following description are only examples of the present disclosure, and for the person skilled in the art, other drawings may be obtained based on the provided drawings without any creative efforts.

Figure 1:
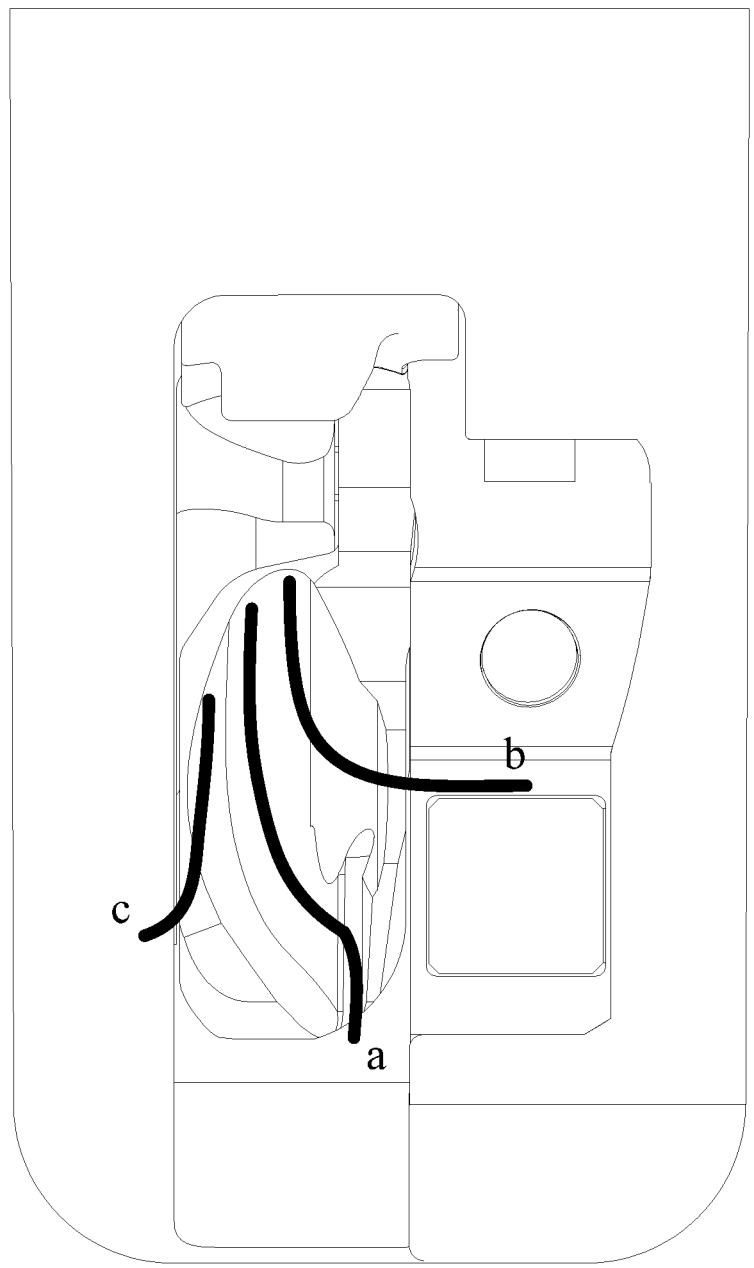
FIG. 1 is a schematic view of three different trajectories of a guide wire in the conventional technologies when the guide wire is extending normally, extending right deflectively and extending left deflectively.

REFERENCE NUMERALS IN FIGURES forceps elevator 1; abutting and fixing member 2; distal end base 3; guide wire 4; positioning bayonet 10; shearing edge 11; guiding surface 12; side edge positioning portion 13; guiding groove 14; first abutting surface 20; second abutting surface 21; first mounting portion 31; first inner side surface 31a; second mounting portion 32; second inner side surface 32a; protruding wall 310; working surface 311; first mounting surface 3111; second mounting surface 3112; third mounting surface 3113; nozzle 312; objective lens 313; lens 314; inclined edge 3100; accommodating space 33; light source apparatus 100; processor apparatus 200; treatment insertion portion 300; operation end 301; endoscopic distal end 302.

DETAILED DESCRIPTION OF THE EMBODIMENTS

The technical solutions according to the embodiments of the present application will be described clearly and completely as follows in conjunction with the drawings in the embodiments of the present application. It is apparent that the described embodiments are only a part of the embodiments according to the present application, rather than all of the embodiments. Based on the embodiments of the present application, all other embodiments obtained without creative efforts by those of ordinary skill in the art shall fall within the scope of protection of the present application.

First Specific Embodiment

Figure 2:
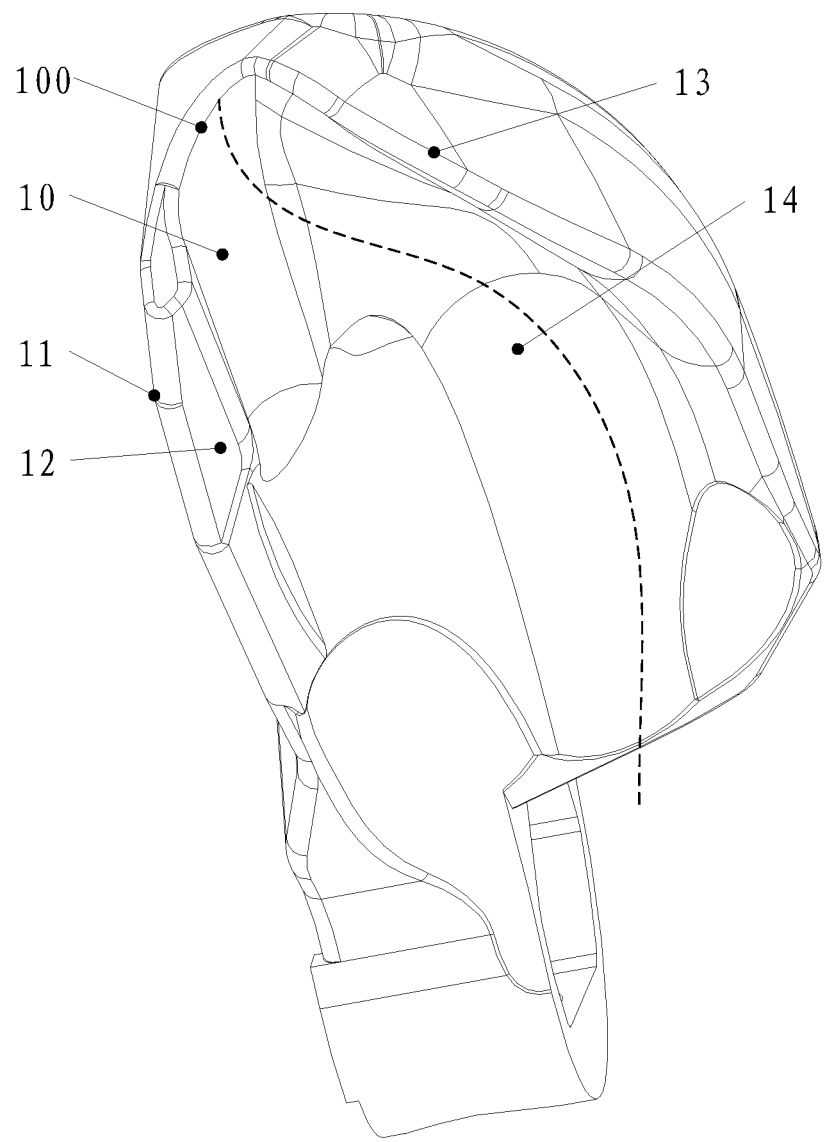
FIG. 2 is a schematic structural view of a forceps elevator provided according to a first specific embodiment of the present disclosure.
Figure 3:
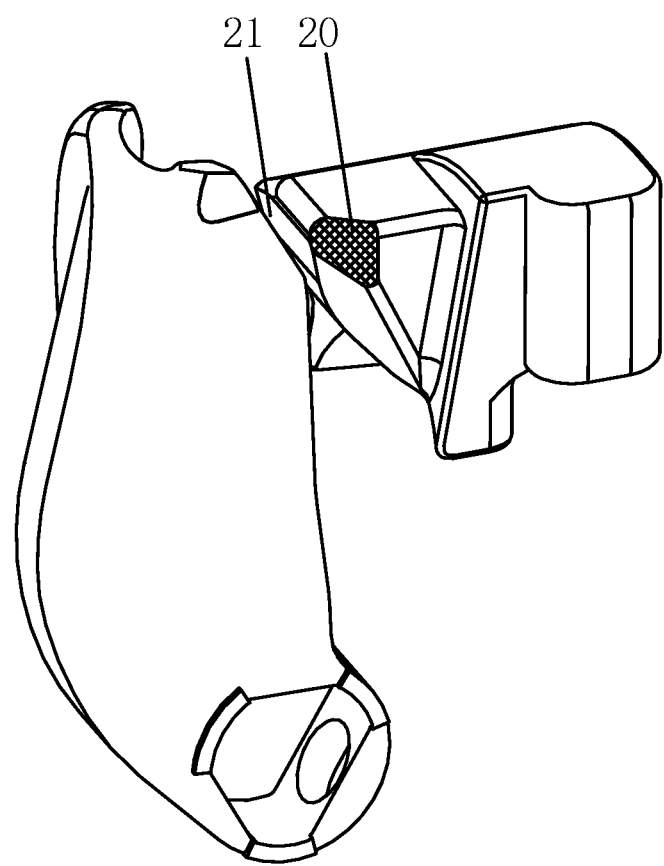
FIG. 3 is a schematic structural view of an abutting and fixing member provided according to a second specific embodiment of the present disclosure.

Referring to FIG. 2, FIG. 2 is a schematic structural view of a forceps elevator provided according to a first specific embodiment of the present disclosure.

An endoscopic forceps elevator is provided according to the first specific embodiment of the present disclosure, where the bottom of the endoscopic forceps elevator is in communication with an instrument channel, and a hinge portion for hinging with a distal end base 3 of an endoscope is arranged at the bottom of the endoscopic forceps elevator; a positioning groove 10 adapted to an instrument to be positioned is arranged at the top of the endoscopic forceps elevator; a shearing edge 11 and a guiding surface 12 are provided at a side edge of the endoscopic forceps elevator, and the guiding surface 12 is located between the positioning groove 10 and the shearing edge 11.

In a case that the instrument to be positioned extends out right deflectively (i.e., "in the first extending-out state"), as the endoscope elevator being lifted; firstly, the shearing edge 11 is configured to move against an inner surface of the distal end base 3 to guide the instrument to be positioned in the right deflective extending-out state onto the guiding surface 12; subsequently, the guiding surface 12 is configured to guide the instrument to be positioned into the positioning groove 10; finally, the positioning groove 10 of the endoscopic forceps elevator is configured to cooperate with the abutting and fixing member 2 to clamp and fix the instrument to be positioned.

It can be seen that in a case that the instrument to be positioned such as a guide wire, a catheter, or other treatment instruments extends out with being deflective, the endoscopic forceps elevator provided according to the present disclosure is configured to adjust the instrument to be positioned back to the positioning groove 10, so as to effectively and accurately clamp and fix the instrument to be positioned, which prevents the instrument to be positioned from coming out of a papilla and being moved to the inside of the papilla, ensuring the successful operation of surgery.

Specifically, in the above endoscopic forceps elevator, an outer notch of the positioning groove 10 is a positioning bayonet 100 located at the top end of the endoscopic forceps elevator; a guiding groove 14 is arranged between the positioning bayonet 100 and the instrument channel and is in communication with the positioning bayonet 100 and the instrument channel, respectively. Before the forceps elevator being lifted, the instrument to be positioned is guided by the guiding groove 14 into the positioning bayonet 100 while being stopped laterally. During a lifting process of the forceps elevator, the guiding surface 12 is configured to guide the instrument to be positioned into the positioning groove 10 and the positioning bayonet 100 for being positioned.

Specifically, in the above endoscopic forceps elevator, the positioning groove 10 is in a strip-shaped groove structure, one side of the positioning groove 10 intersects with the guiding surface 12 to form a first transition edge or transition surface, and the other side of the positioning groove 10 intersects with the guiding groove 14 to form a second transition edge.

Second Specific Embodiment

Figure 4:
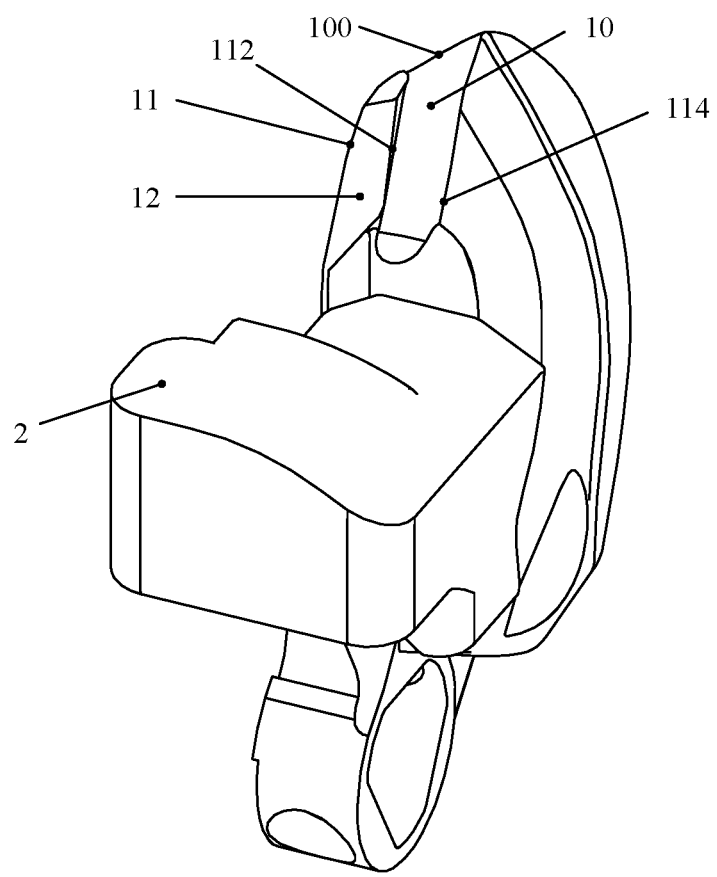
FIG. 4 is a schematic view of a positional relation between the forceps elevator and the abutting and fixing member provided according to the second specific embodiment of the present disclosure after the forceps elevator being lifted.
Figure 5:
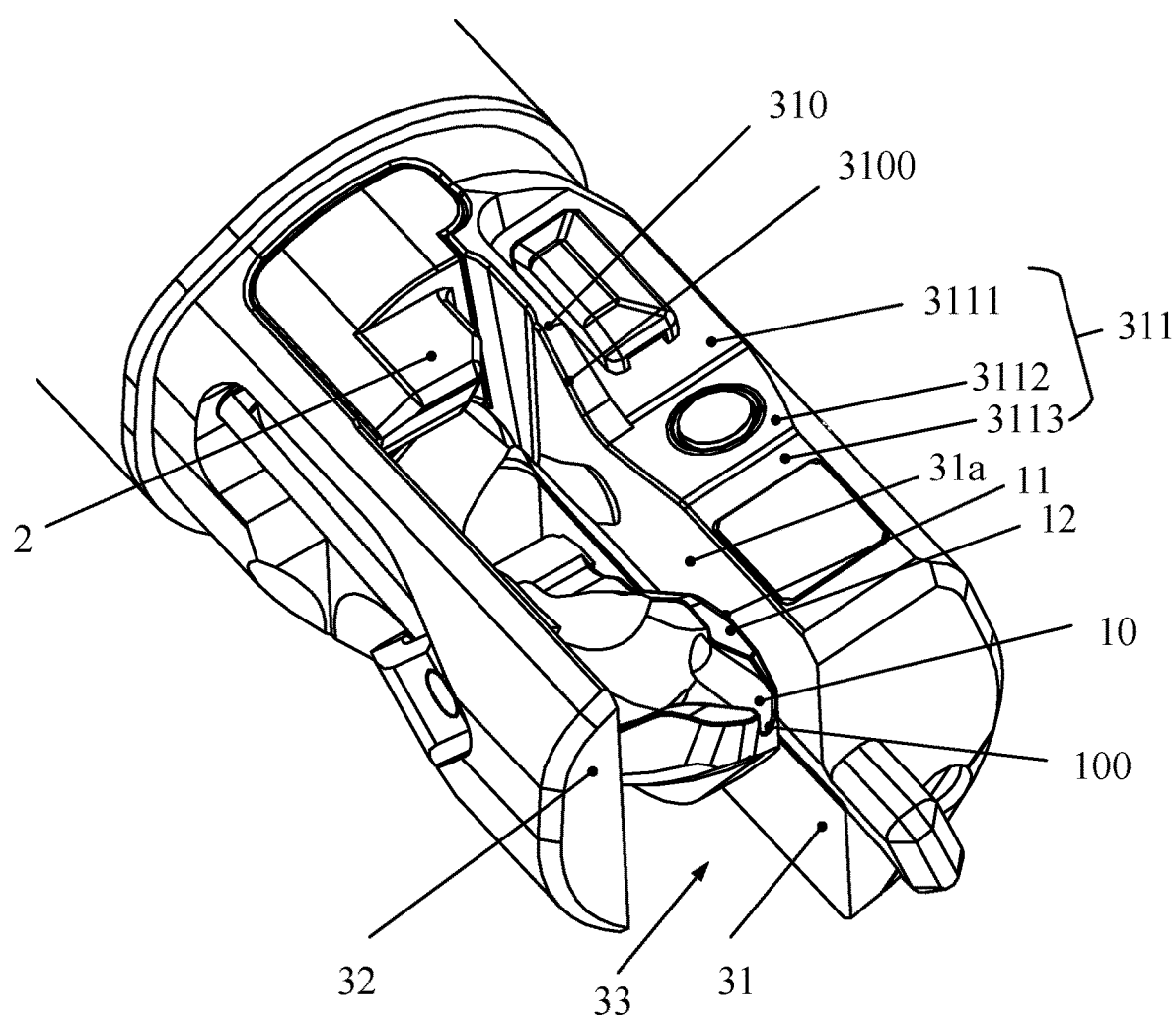
FIG. 5 is a schematic structural view of an endoscopic distal end provided according to the second specific embodiment of the present disclosure.
Figure 6:
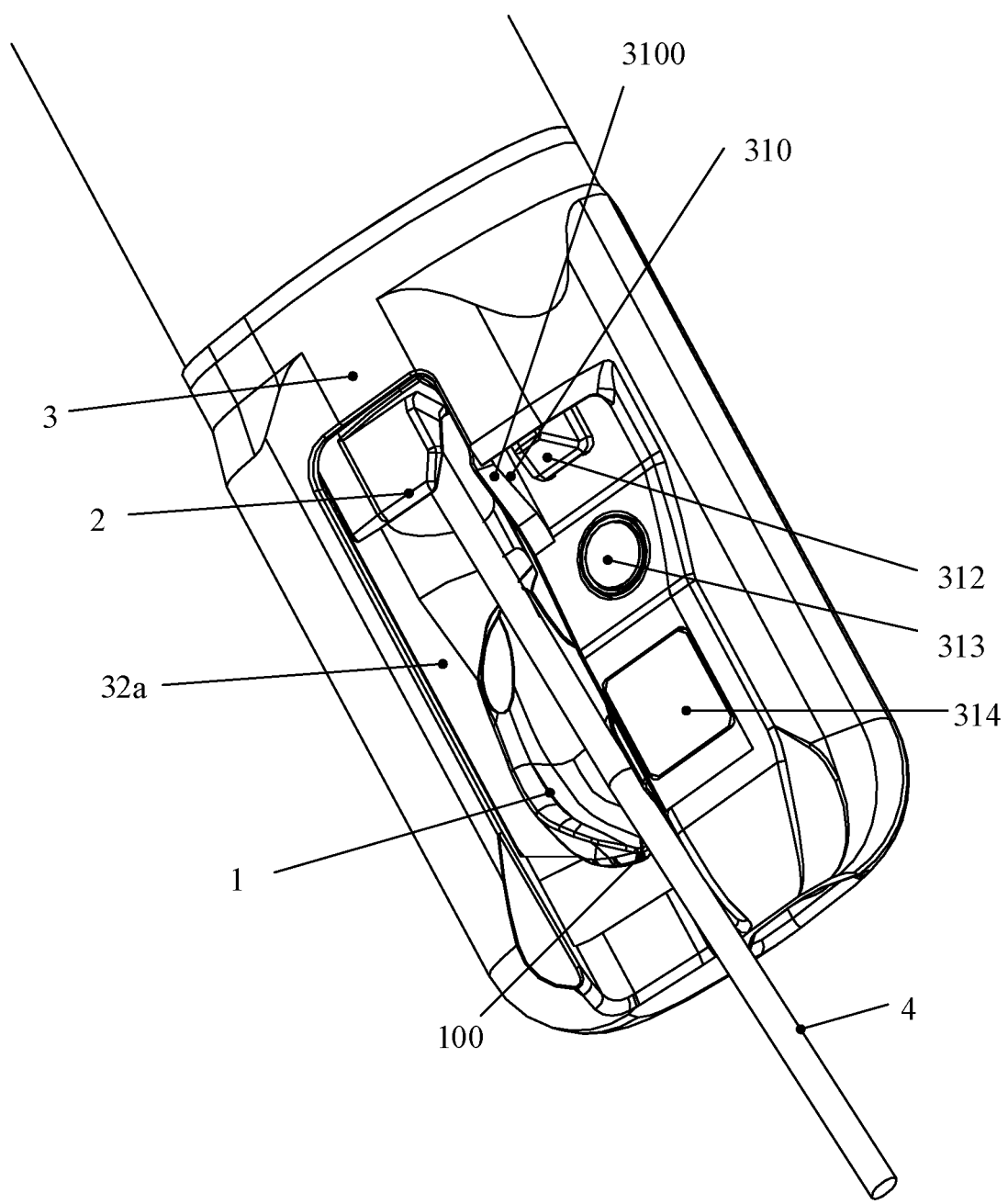
FIG. 6 is a schematic structural view of the guide wire provided according to the second specific embodiment of the present disclosure when the guide wire is extending out normally and positioned by a positioning bayonet of the forceps elevator.
Figure 7:
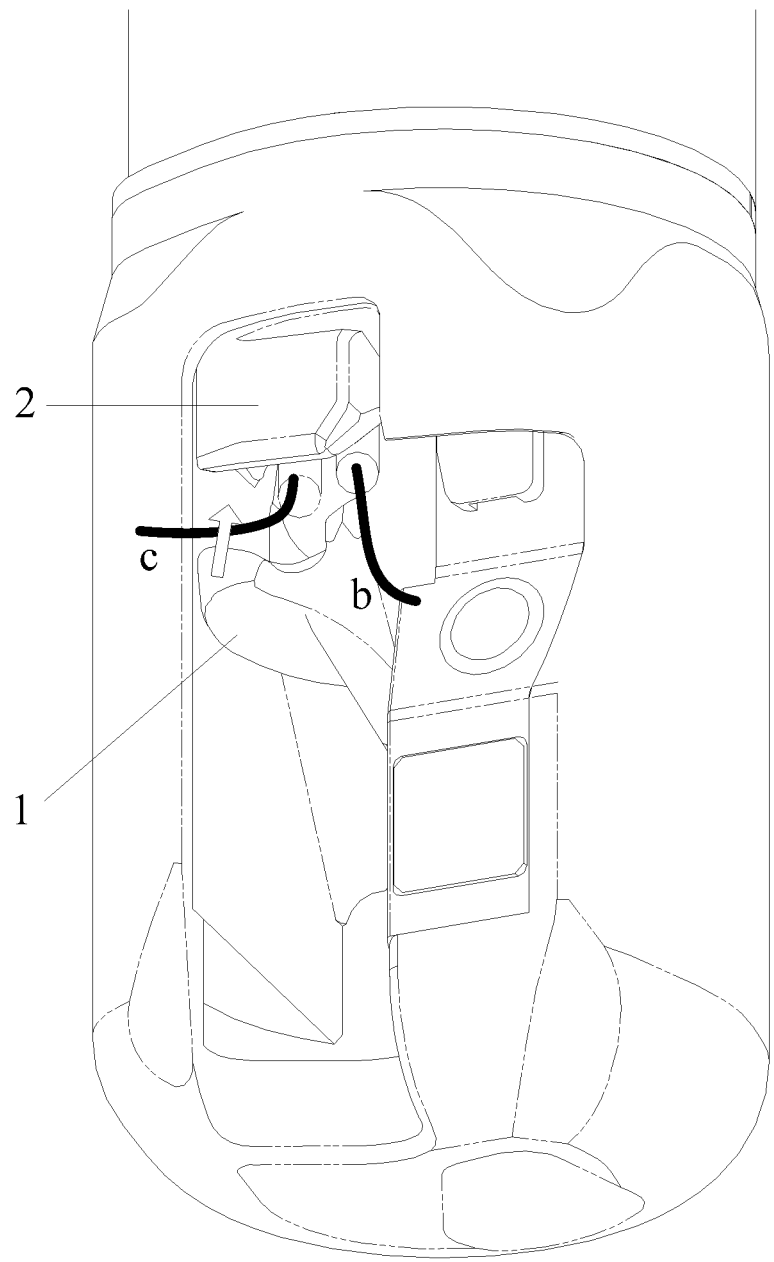
FIG. 7 is a schematic structural view of the forceps elevator provided according to the second specific embodiment of the present disclosure as conducting lifting in cases that the guide wire is extending-out right deflectively and extending-out left deflectively.
Figure 8:
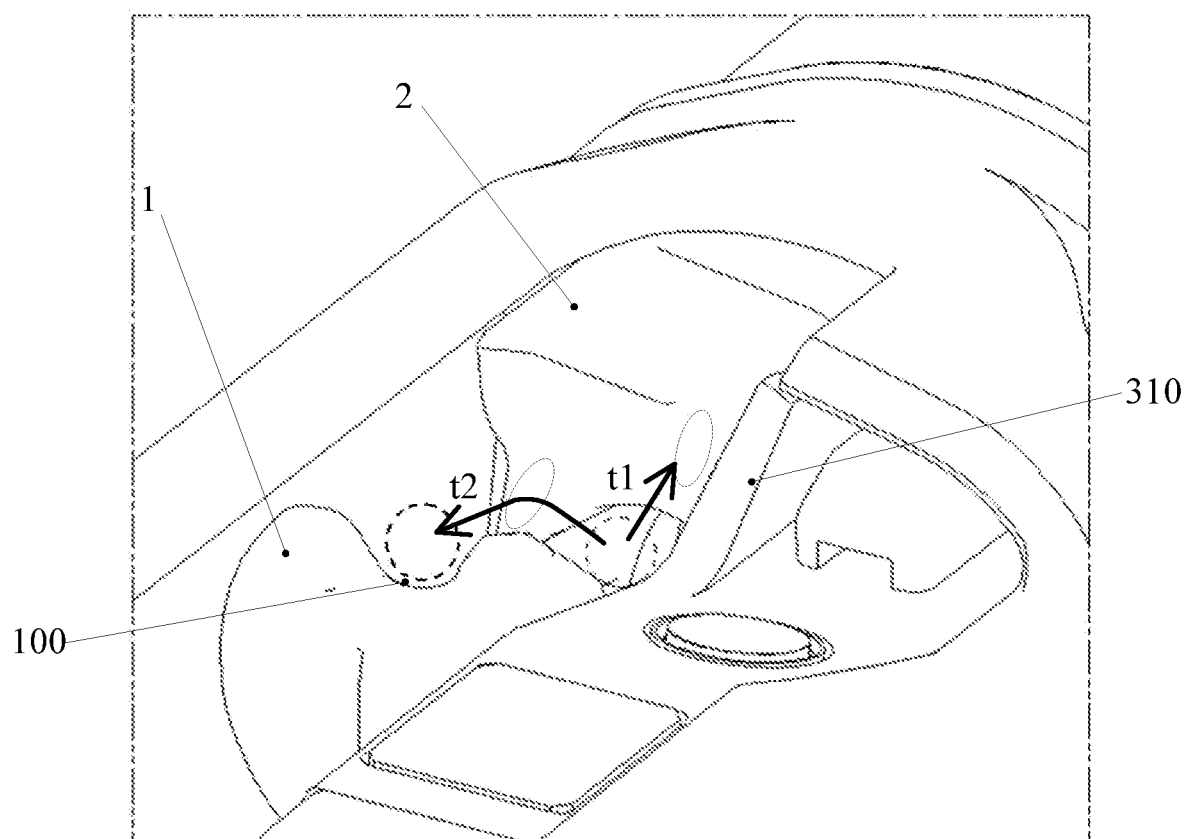
FIG. 8 is a schematic exploded view of a movement trajectory of the guide wire when the guide wire extending out right deflectively is guided into the positioning bayonet of the forceps elevator by a guiding surface of the forceps elevator during the forceps elevator provided according to the second embodiment of the present disclosure being lifted.
Figure 9:
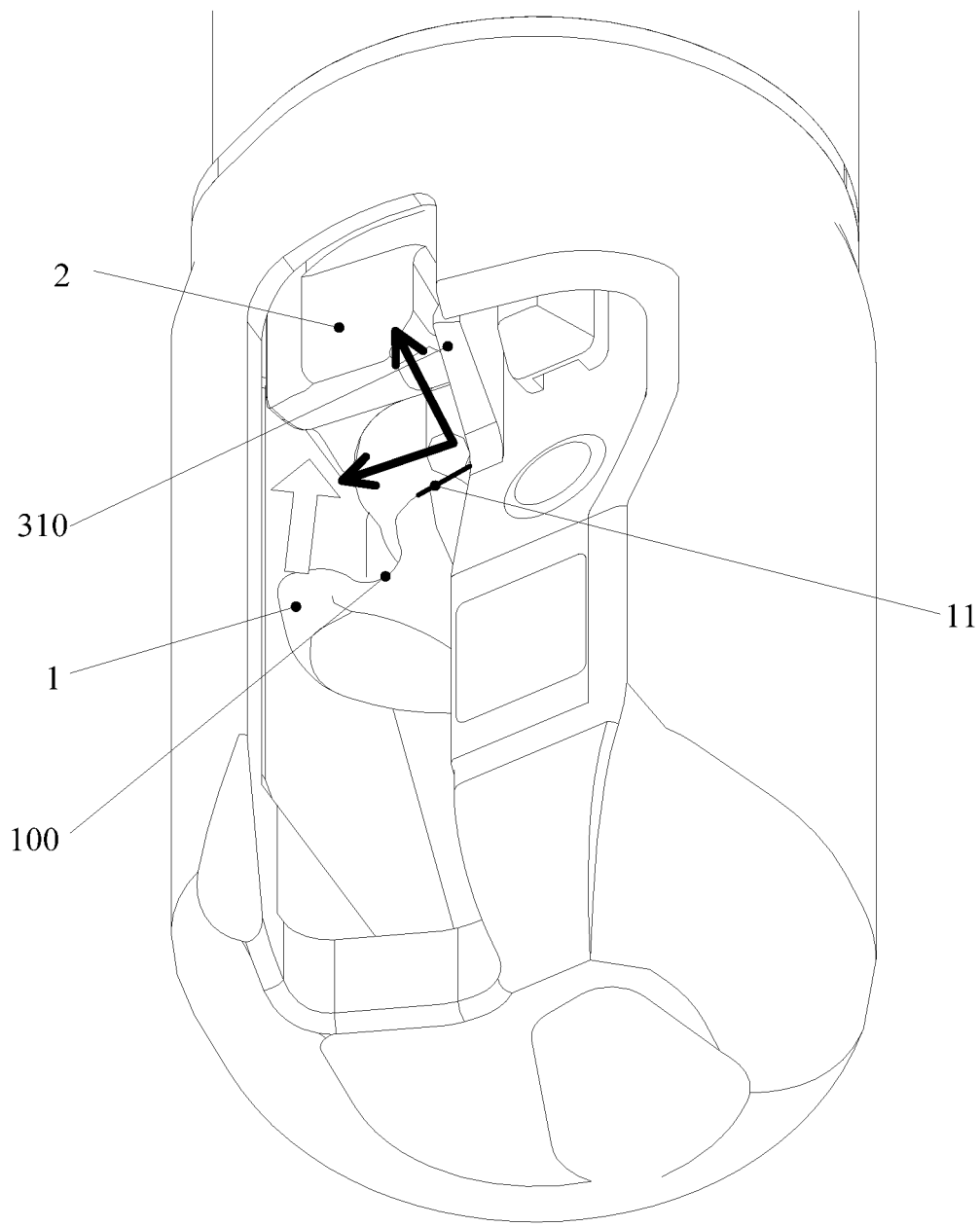
FIG. 9 is a schematic exploded view of a movement direction of the guide wire shown in FIG. 8.
Figure 10:
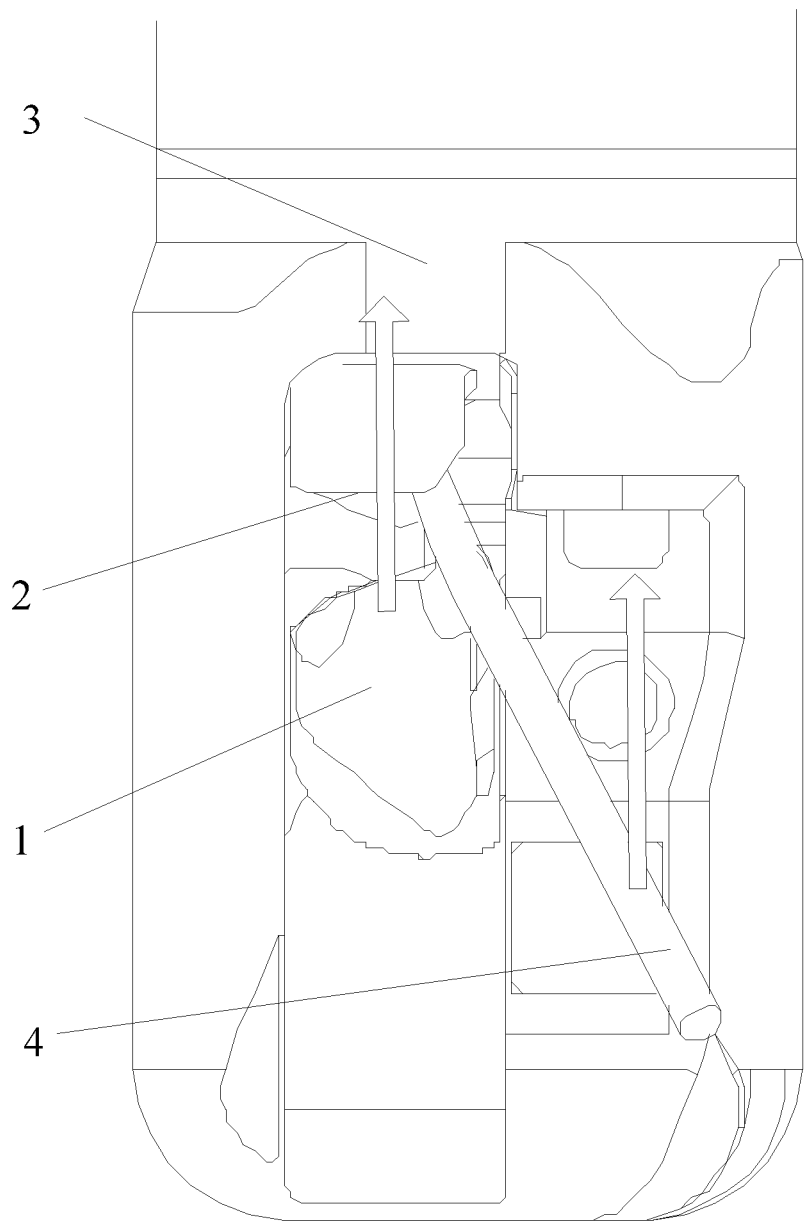
FIG. 10 is another perspective view of FIG. 9.
Figure 11:
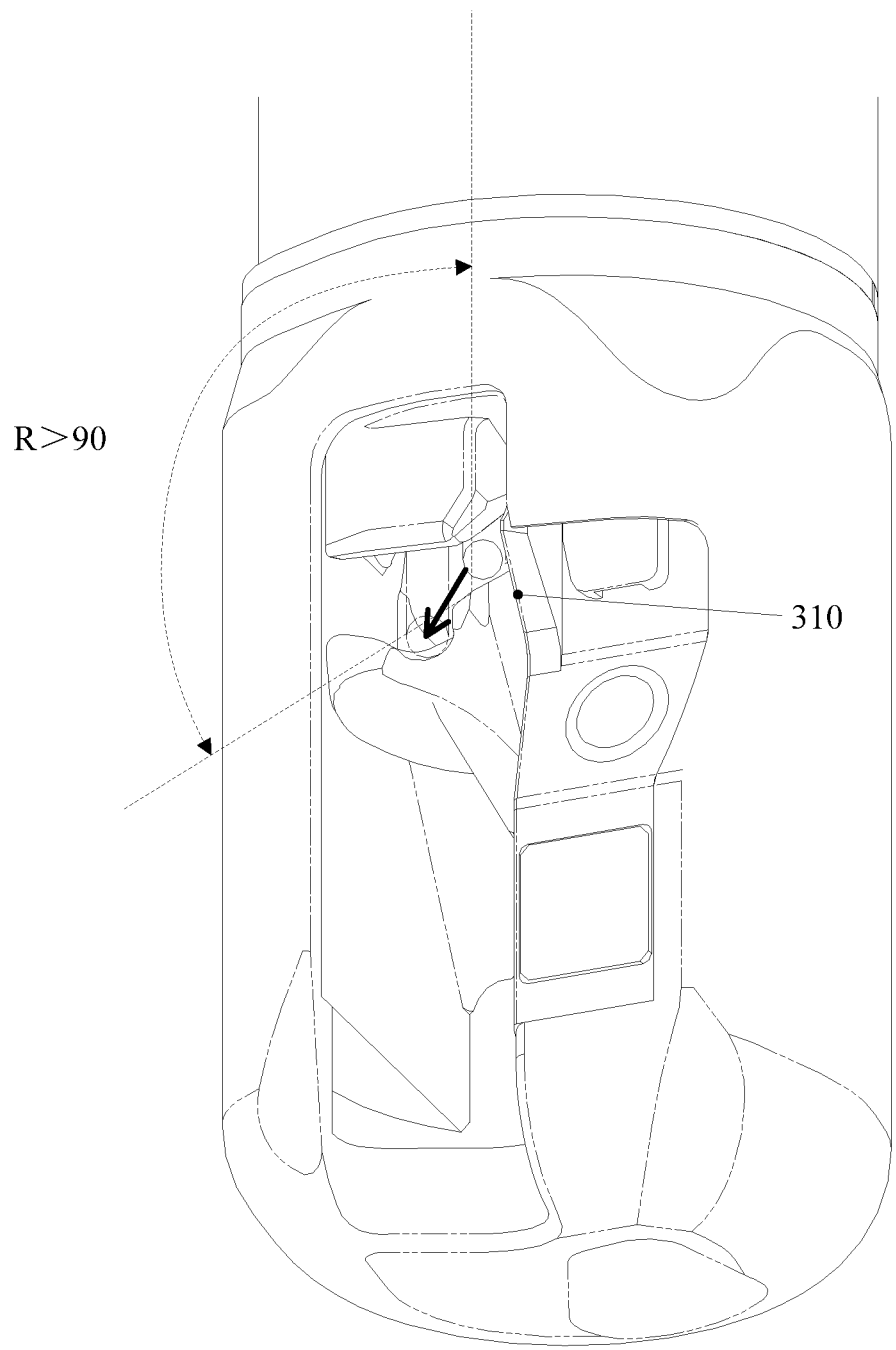
FIG. 11 is a schematic view of an included angle between a plane in which the guiding surface of the forceps elevator is located and an axial direction of the endoscopic distal end shown in FIG. 10.
Figure 12:
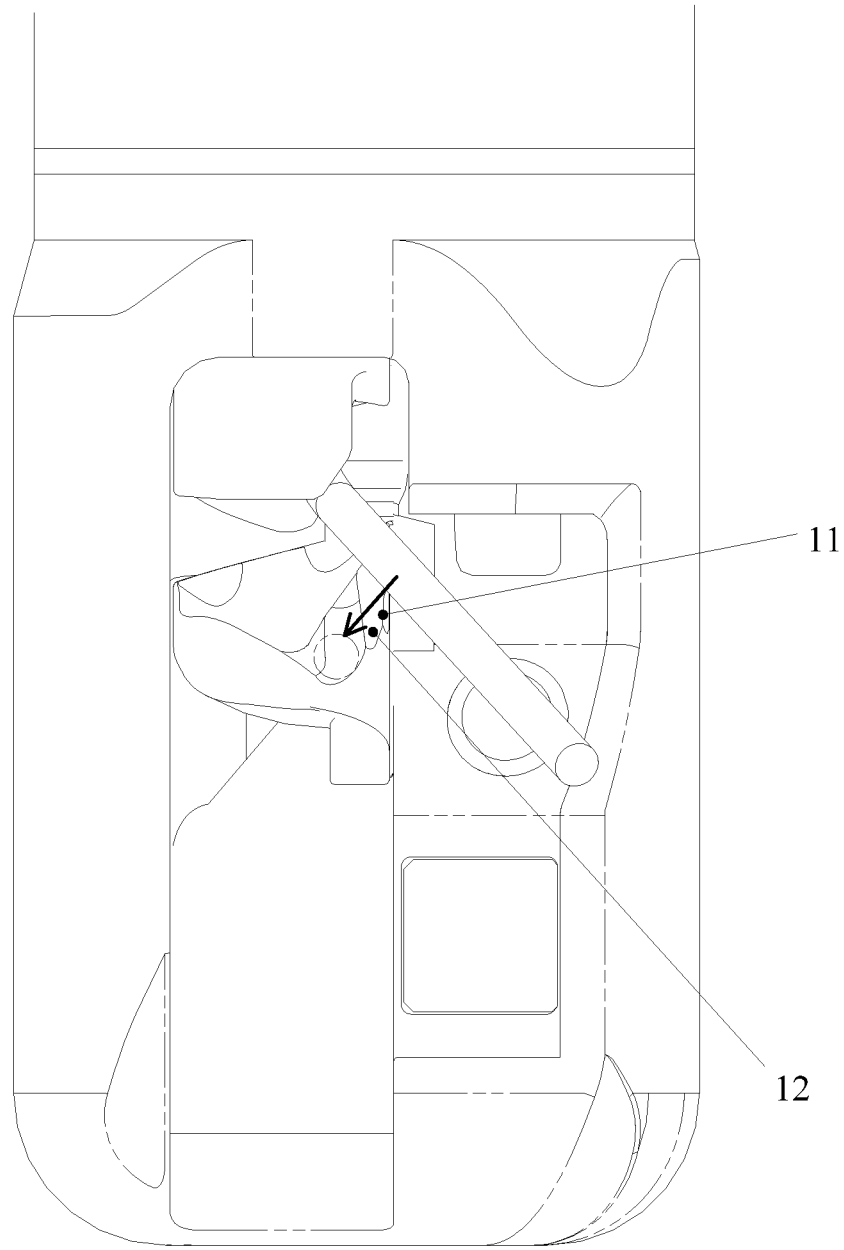
FIG. 12 is another perspective view of FIG. 11.
Figure 13:
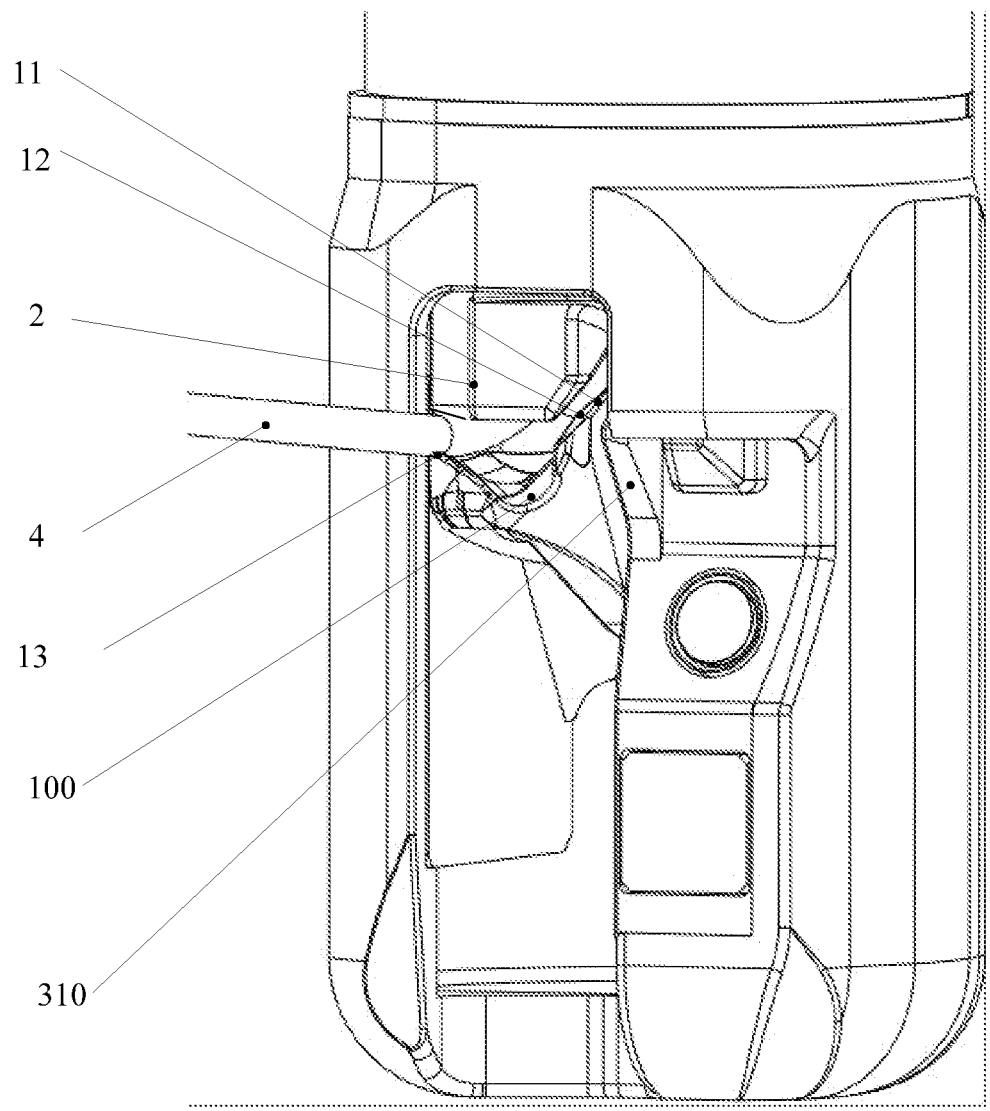
FIG. 13 is a schematic structural view of the guide wire provided according to the second specific embodiment of the present disclosure when the guide wire extend out left deflectively and is clamped and positioned by both the forceps elevator and the abutting and fixing member.

Referring to FIGS. 3 to 13, FIG. 3 is a schematic structural view of an abutting and fixing member provided according to the second specific embodiment of the present disclosure; FIG. 4 is a schematic view of a positional relationship between the forceps elevator and the abutting and fixing member provided according to the second specific embodiment of the present disclosure after a forceps is lifted by the forceps elevator; FIG. 5 is a schematic structural view of an endoscopic distal end provided according to the second specific embodiment of the present disclosure; FIG. 6 is a schematic structural view of the guide wire provided according to the second specific embodiment of the present disclosure when the guide wire is extending out normally and is positioned by a positioning bayonet of the forceps elevator; FIG. 7 is a schematic structural view of the forceps elevator provided according to the second specific embodiment of the present disclosure as conducting lifting in cases that the guide wire is extending-out right deflectively and extending-out left deflectively; FIG. 8 is a schematic exploded view of a movement trajectory of the guide wire when the guide wire extending out right deflectively is guided into the positioning bayonet of the forceps elevator by a guiding surface of the forceps elevator during the forceps elevator lifting the forceps provided according to the second embodiment of the present disclosure; FIG. 9 is a schematic exploded view of a movement direction of the guide wire shown in FIG. 8; FIG. 10 is another perspective view of FIG. 9; FIG. 11 is a schematic view of an included angle between a plane in which the guiding surface of the forceps elevator is located and an axial direction of the endoscopic distal end shown in FIG. 10; FIG. 12 is another perspective view of FIG. 11; FIG. 13 is a schematic structural view of the guide wire provided according to the second specific embodiment of the present disclosure when the guide wire extending-out left deflectively and is clamped and positioned by both the forceps elevator and the abutting and fixing member.

An endoscopic distal end is provided according to the second specific embodiment of the present disclosure. The endoscopic distal end includes a distal end base 3 and a forceps elevator 1, where the forceps elevator 1 is the endoscopic forceps elevator provided according to the first specific embodiment of the present disclosure.

Specifically, referring to FIG. 5, the distal end base 3 in the endoscopic distal end includes a first mounting portion 31, a second mounting portion 32 and an accommodating space 33 for accommodating the forceps elevator 1; the bottom of the accommodating space is configured to be in communication with the instrument channel, and the two sides of the accommodating space are a first inner side surface 31*a* of the first mounting portion 31 and a second inner side surface 32*a* of the second mounting portion 32, respectively.

A front surface of the first mounting portion 31 is a working surface 311 intersecting with the first inner side surface, which is configured for installing functional devices; a protruding wall 310 protruding outside the working surface 311 is provided on the bottom of the working surface 311 close to the accommodating space, and an inner side surface of the protruding wall 310 is coplanar with the first inner side surface, and both of which are inner side surfaces of the distal end base 3.

In a case of extending out from the instrument channel and being right deflectively extending at the bottom of the accommodating space, the instrument to be positioned will contact on the first inner surface of the first mounting portion 31. Since the protruding wall 310 is provided on the first inner side surface to increase an outward extension distance of the first inner side surface of the first mounting portion 31 so as to guide and straighten the instrument to be positioned, it is beneficial to preventing the instrument to be positioned from being bent outwards the first mounting portion 31 and deviating from the center axis of the endoscopic distal end base.

In addition, during the lifting process of the forceps elevator 1, the shearing edge 11 is configured to be moved against the first inner side surface of the first mounting portion 31 and the inner side surface of the protruding wall 310 to a position where the instrument to be positioned extending right deflectively is, and the instrument to be positioned is moved onto the guiding surface 12 by the shearing edge 11. After that, the instrument to be positioned is guided into the positioning groove 10 and the positioning bayonet 100 at the top of the forceps elevator 1 by the guiding surface 12. The positioning bayonet 100 is configured to position (i.e., laterally position-limit) the instrument to be positioned. When the lifting by the forceps elevator reaches to the limit position, the positioning groove 10 of the forceps elevator 1 and the abutting surface 20 of the abutting and fixing member 2 are configured to clamp and fix the instrument to be positioned.

Specifically, as shown in FIGS. 5 and 6, an outer edge of the protruding wall 310 includes an inclined edge 3100 with a gradually decreasing protrusion height, and the part of the inclined edge 3100 with the highest protrusion height is closer to the bottom of the accommodating space than the part of the inclined edge 3100 with the lowest protrusion height.

Therefore, in a case that the instrument to be positioned extends out of the instrument channel and is extending right deflectively at the bottom of the accommodating space, during the lifting of the forceps elevator 1, the shearing edge 11 is configured to be moved against the first inner side surface of the first mounting portion 31 and the inner side surface of the protruding wall 310 to a position where the instrument to be positioned extending right deflectively is. After that, with the forceps elevator 1 being lifted and movement of the shearing edge 11, the instrument to be positioned is moved by the shearing edge onto the guiding surface 12. In addition, at this time, with the forceps elevator 1 being lifted and the movement of the shearing edge 11, the inclined edge 3100 of the protruding wall 310 is configured to gradually straighten the instrument to be positioned. Reference may be made to the movement trajectory of the guide wire shown by the arrow in FIG. 8 for the straightening process. The arrow t1 means that the guide wire is pressed toward the abutting and fixing member 2 during the lifting process of the forceps elevator 1; the arrow t2 means that the guide wire is guided into the positioning bayonet 100 by the shearing edge 11 and the guiding surface 12 on the right side of the forceps elevator.

Specifically, in the working surface 311 of the first mounting portion 31, a first mounting surface 3111, a second mounting surface 3112 and a third mounting surface 3113 are arranged in sequence along the axial direction, where the first mounting surface is located at a radial outer side of the bottom of the accommodating space, the third mounting surface is located at a radial outer side of the top of the accommodating space, and the second mounting surface is an inclined surface located between the first mounting surface and the third mounting surface. In addition, a distance between the first mounting surface and a center plane of the endoscopic distal end is smaller than a distance between the third mounting surface and the center plane of the endoscopic distal end. As shown in the figures, the protruding wall 310 is arranged on the first mounting surface and on a junction between the first mounting surface and the second mounting surface.

Specifically, the functional devices mounted on the working surface 311 of the first mounting portion 31 include a nozzle 312 of a water vapor system, an objective lens 313 of an imaging system, and a lens 314 of an illumination system. The nozzle 312 is mounted on the first mounting surface, the objective lens 313 is mounted on the second mounting surface, and the lens 314 is mounted on the third mounting surface.

Specifically, an included angle between the first inner side surface (i.e., the inner side surface of the first mounting portion 31 in the distal end base 3) and the guiding surface 12 is greater than 90 degrees and less than 180 degrees. Since the first inner side surface is parallel to the center axis of the endoscopic distal end, an included angle between the guiding surface 12 on the forceps elevator 1 and the center axis of the endoscopic distal end is equal to the above included angle between the first inner side surface and the guiding surface. For details, reference may be made to the dotted line and the included angle R in FIG. 11.

Therefore, referring to FIG. 11, in a case that the instrument to be positioned extends out from the right side of the abutting and fixing member 2 and the right side of the forceps elevator 1 (i.e., extending-out right deflectively), and the forceps elevator 1 is lifted by a small angle, the first inner surface of the distal end base 3 and the guiding surface 12 on the forceps elevator 1 form a V-shaped groove to position-limit the guide wire as viewing from the extending-out end of the instrument to be positioned.

Referring to FIGS. 8 and 9, as the forceps elevator 1 being lifted, a guiding movement to the instrument to be positioned can be decomposed into two movements, where one movement is a movement that the instrument to be positioned is straighten along the edge of the protruding wall 310, as shown by the thick arrow inclined upward in FIG. 9; the other movement is a movement that the instrument to be positioned is guided into the positioning bayonet along the guiding surface 12 of the forceps elevator, as shown by the thick arrow inclined leftward in FIG. 9. Therefore, the movement trajectory of the instrument to be positioned on the forceps elevator 1 is as shown in FIG. 8.

Specifically, the abutting and fixing member 2 is located at the bottom of the accommodating space, and an abutting surface of the abutting and fixing member 2 includes a first abutting surface 20 and a second abutting surface 21. The first abutting surface 20 is configured to cooperate with the positioning groove 10 to clamp and fix the instrument to be positioned. The shearing edge 11 is arranged at the right side of the endoscopic forceps elevator, and a side edge positioning portion 13 is arranged at the left side of the endoscopic forceps elevator. After the endoscopic forceps elevator is lifted, the side edge positioning portion 13 is configured to cooperate with the second abutting surface (i.e., the left abutting surface of the abutting and fixing member 2) to clamp and fix the instrument to be positioned extending-out left deflectively (i.e., in a second deflective extending-out state).

Further, the second abutting surface on the abutting and fixing member 2 and the second inner surface on the distal end base 3 form a clamping groove for accommodating the side edge positioning portion 13 of the forceps elevator 1.

As shown in FIG. 13, in a case that the instrument to be positioned extends out from the left side of the abutting and fixing member 2 and the left side of the forceps elevator 1, after the forceps elevator 1 is lifted, the instrument to be positioned is abutted against the side edge positioning portion 13 to be fixed in the clamping groove so as to form a two-point clamping.

Specifically, an included angle between the first abutting surface 20 on the abutting and fixing member 2 and the center axis of the endoscopic distal end is greater than zero.

Specifically, the first abutting surface 20 on the abutting and fixing member 2 may be a flat surface, a curved surface or a stepped surface; and the second abutting surface on the abutting and fixing member 2 may be a flat surface, a curved surface or a stepped surface.

Third Specific Embodiment

Figure 14:
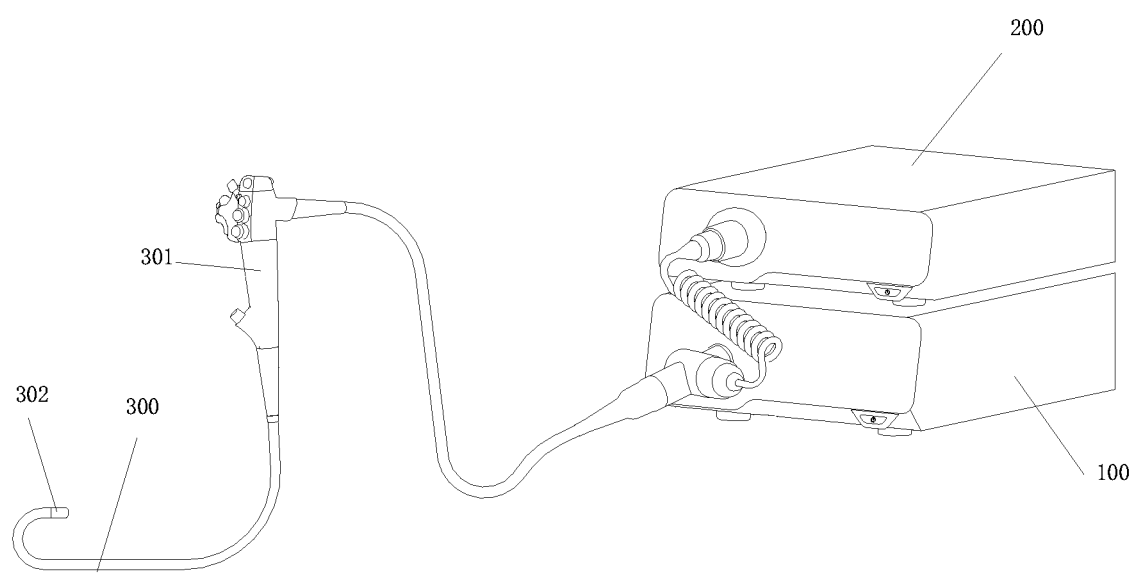
FIG. 14 is a schematic structural view of a duodenoscope system provided according to a third embodiment of the present disclosure.

Reference is made to FIG. 14, which is a schematic structural view of a duodenoscope system provided according to the third embodiment of the present disclosure.

A duodenoscope system is provided according to the third specific embodiment of the present disclosure, where an endoscope of the duodenoscope system is provided with the endoscopic distal end provided according to the second specific embodiment of the present disclosure.

The duodenoscope system includes an endoscope portion, a light source portion 100 and a host portion 200, where the endoscope generally includes an insertion portion 300 for inserting into a body cavity to be checked, and one end of the insertion portion 300 is an endoscopic distal end 302, the other end is an operation end 301. A forceps elevator is provided in the endoscopic distal end 302, and the operation end 301 is provided with a lever for controlling the lifting and lowering of the forceps elevator. The light source portion 100 is configured to provide white light illumination and special light illumination for the endoscope, and the host portion 200 is configure to provide signal control for the endoscope and to process images captured by the endoscope, where the host portion 200 is connected to a display to realize the display of endoscopic images.

Specifically, the endoscopic distal end base in the above endoscopic distal end 302 is further provided with a nozzle 312 of a water vapor system, an objective lens 313 of an imaging system and a lens 314 of an illumination system, where the nozzle 312 is configured to spray fluids such as water or air onto an outer surface of the objective lens 313 to clean the objective lens 313. An imaging element CCD of an observation optical system is arranged on an inner side of the objective lens of the imaging system, which is configured to send the image information captured by the insertion portion back to the host portion for display. The lens 314 is connected to an optical fiber served as a light transmission path.

Further, a distal end cap is covered on the endoscopic distal end base, and the distal end cap is detachably connected to the distal end base.

It should be noted here that the "left" and "right" mentioned herein are all exemplified with reference to FIGS. 5 to 13. In other specific embodiments, the endoscopic distal end may also be provided as a left-right symmetrical structure with the endoscopic distal end provided according to the second specific embodiment of the present disclosure, and the function and effect of which remain unchanged. In this case, the instrument to be positioned being in the first deflective extending-out state means that the instrument to be positioned extends out left deflectively, and the instrument to be positioned being in the second deflective extending-out state means that the instrument to be positioned extends out right deflectively. Reference may be made to the above specific implementation for other structures, which will not be described herein.

Finally, it should be further noted that a relation term such as "first" and "second" herein is only used to distinguish one entity or operation from another entity or operation, and does not necessarily require or imply that there is an actual relation or sequence between these entities or operations. Moreover, the terms "comprise", "include", or any other variants thereof are intended to encompass a non-exclusive inclusion, such that the process, method, article, or device including a series of elements includes not only those elements but also those elements that are not explicitly listed, or the elements that are inherent to such process, method, article, or device. Unless explicitly limited, the statement "including a . . . " does not exclude the case that other similar elements may exist in the process, the method, the article or the device other than enumerated elements.

The above embodiments are described in a progressive manner. Each of the embodiments is mainly focused on describing its differences from other embodiments, and reference may be made among these embodiments with respect to the same or similar parts.

The above illustration of the disclosed embodiments can enable those skilled in the art to implement or use the present disclosure. Various modifications to the embodiments are apparent to the person skilled in the art, and the general principle herein can be implemented in other embodiments without departing from the spirit or scope of the present application. Therefore, the present application is not limited to the embodiments described herein, but should be in accordance with the broadest scope consistent with the principle and novel features disclosed herein.

The invention claimed is:

1. An endoscopic forceps elevator, wherein a bottom of the endoscopic forceps elevator is in communication with an instrument channel, and a hinge portion for hinging with a distal end base of an endoscope is arranged at the bottom of the endoscopic forceps elevator;
   a positioning groove adapted to an instrument to be positioned is arranged at the top of the endoscopic forceps elevator;
   a shearing edge and a guiding surface are provided at a side edge of the endoscopic forceps elevator, and the guiding surface is located between the positioning groove and the shearing edge;
   during a lifting process of the endoscopic forceps elevator, the shearing edge is moveable against an inner surface of the distal end base to guide the instrument to be positioned in a first deflective extending-out state onto the guiding surface; the guiding surface is configured to guide the instrument to be positioned into the positioning groove, and the positioning groove is configured to cooperate with an abutting and fixing member to clamp and fix the instrument to be positioned.

2. The endoscopic forceps elevator according to claim 1, wherein an outer notch of the positioning groove is a positioning bayonet located at the top end of the endoscopic forceps elevator;
   a guiding groove in communication with the positioning bayonet and the instrument channel, respectively, is arranged between the positioning bayonet and the instrument channel; before the endoscopic forceps elevator being lifted, the instrument to be positioned is guided into the positioning bayonet by the guiding groove and position-limited laterally.

3. The endoscopic forceps elevator according to claim 2, wherein the positioning groove is in a strip-shaped groove structure, one side of the positioning groove intersects with the guiding surface to form a first transition edge or a transition surface, and the other side of the positioning groove intersects with the guiding groove to form a second transition edge.

4. An endoscopic distal end, comprising a distal end base and a forceps elevator, wherein a bottom of the forceps elevator is in communication with an instrument channel, and a hinge portion for hinging with the distal end base of an endoscope is arranged at the bottom of the forceps elevator;
   a positioning groove adapted to an instrument to be positioned is arranged at the top of the forceps elevator;
   a shearing edge and a guiding surface are provided at a side edge of the forceps elevator, and the guiding surface is located between the positioning groove and the shearing edge;
   during a lifting process of the forceps elevator, the shearing edge is moveable against an inner surface of the distal end base to guide the instrument to be positioned in a first deflective extending-out state onto the guiding surface; the guiding surface is configured to guide the instrument to be positioned into the positioning groove, and the positioning groove is configured to cooperate with an abutting and fixing member to clamp and fix the instrument to be positioned.

5. The endoscopic distal end according to claim 4, wherein the distal end base comprises a first mounting portion, a second mounting portion and an accommodating space for accommodating the forceps elevator; the bottom of the accommodating space is in communication with the instrument channel, and the two sides of the accommodating space are a first inner side surface of the first mounting portion and a second inner side surface of the second mounting portion, respectively; a front surface of the first mounting portion is a working surface for installing functional devices, and the working surface intersects with the first inner side surface; a protruding wall protruding outside the working surface is provided on the bottom of the working surface close to the accommodating space, the protruding wall extends beyond the abutting and fixing member in a direction away from the bottom of the accommodating space, and an inner side surface of the protruding wall is coplanar with the first inner side surface, both of which are inner side surfaces of the distal end base;

during a lifting process of the forceps elevator, the shearing edge is movable against the inner side surface of the protruding wall to guide the instrument to be positioned in the first deflective extending-out state onto the guiding surface.

6. The endoscopic distal end according to claim 5, wherein an outer edge of the protruding wall comprises an inclined edge with a gradually decreasing protrusion height, and a part of the inclined edge with the highest protrusion height is closer to the bottom of the accommodating space than a part of the inclined edge with the lowest protrusion height, at least part of the inclined edge is located at a side of the abutting and fixing member opposite to the bottom of the accommodating space.

7. The endoscopic distal end according to claim 5, wherein a first mounting surface, a second mounting surface and a third mounting surface are arranged on the working surface in sequence along the axial direction;

the first mounting surface is located at a radial outer side of the bottom of the accommodating space;

the third mounting surface is located at a radial outer side of the top of the accommodating space;

the second mounting surface is an inclined surface located between the first mounting surface and the third mounting surface;

a distance between the first mounting surface and a center plane of the endoscopic distal end is smaller than a distance between the third mounting surface and the center plane of the endoscopic distal end, and the protruding wall is provided on the first mounting surface.

8. The endoscopic distal end according to claim 7, wherein the functional devices comprise:

a nozzle of a water vapor system, which is mounted on the first mounting surface;

an objective lens of an imaging system, which is mounted on the second mounting surface;

a lens of an illumination system, which is mounted on the third mounting surface.

9. The endoscopic distal end according to claim 5, wherein the abutting and fixing member is located at the bottom of the accommodating space, and an abutting surface of the abutting and fixing member includes a first abutting surface and a second abutting surface;

the first abutting surface is configured to cooperate with the positioning groove to clamp and fix the instrument to be positioned;

the shearing edge is arranged at one side of the endoscopic forceps elevator, and a side edge positioning portion is arranged at the other side of the endoscopic forceps elevator; after the endoscopic forceps elevator being lifted, the side edge positioning portion is configured to cooperate with the second abutting surface to clamp and fix the instrument to be positioned in a second deflective extending-out state.

10. The endoscopic distal end according to claim 9, wherein the second abutting surface and the second inner side surface form a clamping groove for accommodating the side edge positioning portion; in a case that the instrument to be positioned is in the second deflective extending-out state, after the forceps elevator being lifted, the instrument to be positioned is configured to be abutted against the side edge positioning portion so as to be fixed in the clamping groove.

11. The endoscopic distal end according to claim 10, wherein an included angle between the first abutting surface and a center axis of the endoscopic distal end is greater than zero.

12. The endoscopic distal end according to claim 10, wherein the second abutting surface is a flat surface, a curved surface, or a stepped surface.

13. The endoscopic distal end according to claim 4, wherein the distal end base comprises a first mounting portion, a second mounting portion and an accommodating space for accommodating the forceps elevator; the bottom of the accommodating space is in communication with the instrument channel, and the two sides of the accommodating space are a first inner side surface of the first mounting portion and a second inner side surface of the second mounting portion, respectively;

the inner side surface of the distal end base comprises the first inner side surface of the first mounting portion; and an included angle between the first inner side surface of the first mounting portion and the guiding surface is greater than 90 degrees and less than 180 degrees.

14. A duodenoscope system, comprising the endoscopic distal end according to claim 4.

15. The duodenoscope system according to claim 14, wherein the distal end base comprises a first mounting portion, a second mounting portion and an accommodating space for accommodating the forceps elevator; the bottom of the accommodating space is in communication with the instrument channel, and the two sides of the accommodating space are a first inner side surface of the first mounting portion and a second inner side surface of the second mounting portion, respectively; a front surface of the first mounting portion is a working surface for installing functional devices, and the working surface intersects with the first inner side surface; a protruding wall protruding outside the working surface is provided on the bottom of the working surface close to the accommodating space, the protruding wall extends beyond the abutting and fixing member in a direction away from the bottom of the accommodating space, and an inner side surface of the protruding wall is coplanar with the first inner side surface, both of which are inner side surfaces of the distal end base;

during a lifting process of the forceps elevator, the shearing edge is movable against the inner side surface of the protruding wall to guide the instrument to be positioned in the first deflective extending-out state onto the guiding surface.

16. The duodenoscope system according to claim 15, wherein an outer edge of the protruding wall comprises an inclined edge with a gradually decreasing protrusion height, and a part of the inclined edge with the highest protrusion height is closer to the bottom of the accommodating space than a part of the inclined edge with the lowest protrusion height, at least part of the inclined edge is located at a side of the abutting and fixing member opposite to the bottom of the accommodating space.

17. The duodenoscope system according to claim 15, wherein a first mounting surface, a second mounting surface and a third mounting surface are arranged on the working surface in sequence along the axial direction;

the first mounting surface is located at a radial outer side of the bottom of the accommodating space;
the third mounting surface is located at a radial outer side of the top of the accommodating space;
the second mounting surface is an inclined surface located between the first mounting surface and the third mounting surface;

a distance between the first mounting surface and a center plane of the endoscopic distal end is smaller than a distance between the third mounting surface and the center plane of the endoscopic distal end, and the protruding wall is provided on the first mounting surface.

18. The duodenoscope system according to claim 15, wherein the abutting and fixing member is located at the bottom of the accommodating space, and an abutting surface of the abutting and fixing member includes a first abutting surface and a second abutting surface;

the first abutting surface is configured to cooperate with the positioning groove to clamp and fix the instrument to be positioned;
the shearing edge is arranged at one side of the endoscopic forceps elevator, and a side edge positioning portion is arranged at the other side of the endoscopic forceps elevator; after the endoscopic forceps elevator being lifted, the side edge positioning portion is configured to cooperate with the second abutting surface to clamp and fix the instrument to be positioned in a second deflective extending-out state.

19. The endoscopic distal end according to claim 4, wherein an outer notch of the positioning groove is a positioning bayonet located at the top end of the endoscopic forceps elevator;

a guiding groove in communication with the positioning bayonet and the instrument channel, respectively, is arranged between the positioning bayonet and the instrument channel; before the endoscopic forceps elevator being lifted, the instrument to be positioned is guided into the positioning bayonet by the guiding groove and position-limited laterally.

20. The endoscopic distal end according to claim 19, wherein the positioning groove is in a strip-shaped groove structure, one side of the positioning groove intersects with the guiding surface to form a first transition edge or a transition surface, and the other side of the positioning groove intersects with the guiding groove to form a second transition edge.

* * * * *